United States Patent [19]

Bonaldi et al.

[11] 4,404,199

[45] Sep. 13, 1983

[54] SALIFICATION PRODUCTS OF CHOLIC ACIDS WITH TRIMETHOXY-3,4,5-BENZOIC ESTER OF 2-PHENYL-2-DIMEN-THYLAMINOBUTANOL, HAVING PHARMACOTHERAPEUTIC ACTION, PROCESS FOR THEIR PREPARATION AND THERAPEUTIC COMPOSITIONS CONTAINING THEM AS ACTIVE PRINCIPLE

[75] Inventors: Antonio Bonaldi, Chiuduno; Egidio Molinari, Longone Al Segrino; Vanna Springolo, Milan, all of Italy

[73] Assignee: Erregierre S.p.A., Bergamo, Italy

[21] Appl. No.: 374,243

[22] Filed: May 3, 1982

[30] Foreign Application Priority Data

May 21, 1981 [IT] Italy ............................... 21867 A/81

[51] Int. Cl.$^3$ ............................................. A61K 31/56
[52] U.S. Cl. .................................. 424/238; 260/397.1

[58] Field of Search ...................... 424/238; 260/397.1

[56] References Cited

U.S. PATENT DOCUMENTS

| | | | |
|---|---|---|---|
| 4,022,806 | 5/1977 | Frost et al. | 260/397.1 |
| 4,186,143 | 1/1980 | Ziegler et al. | 260/397.1 |
| 4,241,047 | 12/1980 | Lechevin et al. | 260/397.1 |

Primary Examiner—Elbert L. Roberts
Attorney, Agent, or Firm—Stevens, Davis, Miller & Mosher

[57] ABSTRACT

Salification products between cholic acids (chenodeoxicholic and ursodeoxycholic acid) and trimebutyne in the molar ratio 1:1 or 2:1 have been prepared. These new salts show a pharmacotherapeutic action, which, as a whole, is not found in other known drugs, and which makes them useful for the treatment of diskinesiae, biliary dyspepsiae, cholecystopathies, and for the normalization of the kinesis of the intestinal gastro-biliary tract.

11 Claims, No Drawings

SALIFICATION PRODUCTS OF CHOLIC ACIDS WITH TRIMETHOXY-3,4,5-BENZOIC ESTER OF 2-PHENYL-2-DIMENTHYLAMINOBUTANOL, HAVING PHARMACOTHERAPEUTIC ACTION, PROCESS FOR THEIR PREPARATION AND THERAPEUTIC COMPOSITIONS CONTAINING THEM AS ACTIVE PRINCIPLE

This invention refers to new products of salification of cholic acids with the trimethoxy-3,4,5-benzoic ester of 2-phenyl-2-dimethylaminobutanol(trimebutyne), having a pharmacotherapeutic action.

It is known that cholic acids, especially chenodeoxycholic acid and ursodeoxycholic acid, are used for the treatment of biliary diskinesiae. It is also known that trimebutyne too is used in human therapy for the treatment of alterations of the gastro-intestinal kinesis.

We have now found, and this is the subject-matter of the present invention, that the salification products of cholic acids with trimebutyne act on both biliary diskenesiae and kinesis alterations of the gastrointestinal tract; moreover, both activities are much more increased, compared with those of the starting products.

As a consequence, the new salts we have prepared are to be considered wholly new, even from the point of view of their use in human therapy. They have a range of therapeutic properties which are not found in other drugs that are at present available on the market.

Our salts are particularly useful for the treatment of diskinesiae, biliary dyspepsiae, cholecystopathies, and for the normalization of the kinesis of the gastro-intestinal tract.

The compounds of the present invention, include both trimebutyne simple salts with cholic acids, in which the two components have a molar ratio of 1:1, and complex salts incorporating trimebuthyne and cholic acids, with a molarity ratio of 1:2.

From the point of view of their application, these salts do not show any significant difference. In this new invention, the process by which the new trimebutyne salts with cholic acids are prepared, is as follows:
both the base and the chosen cholic acid—in the desired stoichiometric quantities—are dissolved in appropriate polar solvents or polar solvent mixtures and heated at temperatures ranging from 40° to 100° C.

Then, the products formed out of these solutions are crystallized by vacuum concentration and cooling or by dilution of the solutions with poorly polar solvents and water, and by total or partial elimination of the solvent (1).

In the present invention, polar solvents are preferably chosen among the group composed by water, tetrahydrofuran, methyl alcohol, ethanol, acetone, 1,4-dioxane and their mixtures.

Poorly polar solvents used as precipitants are preferably chosen among the group composed by aliphatic hydrocarbons $C_5-C_8$-.

EXAMPLE 1

38.75 g of trimebutyne and 39.26 g of ursodeoxicholic acid are dissolved in 200 ml of tetrahydrofuran preheated at 50° C. under continuous agitation. After 20 minutes of reaction at such temperature, the solution is cooled to ambient temperature. Then, always under strong agitation, 500 ml of distilled water are added. The obtained solution is kept under agitation for two hours, and then evaporated in a rotating evaporator, until about 300 ml of distillate are removed.

The concentrated solution is cooled at 5°–10° C. under agitation and kept at such temperature, always under agitation, for 3 hours, in order to permit the crystallization of the product, which is collected by filtration on a Buchner funnel, washed with 100 ml of cold distillated water and lastly vacuum dried at a temperature not higher than 50° C. 71 g of white crystalline product are obtained, having the following characteristics: soluble in methyl alcohol, ethanol, acetone; poorly soluble in chloroform, and ethyl acetate; practically insoluble in cyclohexane, diethyl ether, and water. $[\alpha]_{20}\cdot^D$: +28° C. (c=2% in 99%-ethanol).

Ultimate analysis: calculated—C 70,83%, H 8,92%, N 1,80%; found—C 71,5%, H 9,02%, N 1,67%.

m.p.=78°–80° C.

EXAMPLE 2

50 g of ursodeoxycholic acid are added under agitation to a solution of 60 g of trimebutyne in 300 ml of tetrahydrofuran, pre-heated at the temperature of 50° C. The agitation is kept going for 20 minutes, always at the same temperature.

500 ml of isooctane are added to the solution, which is cooled at ambient temperature and agitated for 2 hours, then evaporated in an evaporator, until about 400 ml of distillate are removed.

The concentrated solution is cooled at 5°–10° C. under agitation for 3 hours, in order to permit the crystallization of the product, which is collected by filtration on a Buchner funnel, washed with 100 ml of cold distilled water, and lastly vacuum dried at temperatures not higher than 50° C. 69 g of white crystalline product are obtained, having the same characteristics as the one described in the example 1.

EXAMPLE 3

78,5 g of ursodeoxycholic acid are added to a solution of 38,7 g of trimebutyne in 400 ml of 95% ethanol, pre-heated at about 40° C. The salification is kept going at this temperature for about 30 minutes.

1000 ml of distilled water are slowly added to the strongly agitated solution.

Then the solution is cooled under agitation at +5° C. A white, crystalline precipitate is obtained, then collected on a Buchner funnel, washed with 40%-ethanol and vacuum oven dried at 50%.

102 g of product are obtained having the following characteristics:

$[\alpha]_{20}\cdot^D$: +40° (c=2% in 99%-ethanol)

Ultimate analysis: calculated—C 71,64%, H 9,29%, N 1,19%; found—C 72,01%, H 9,02%, N ;b 1,30%.

EXAMPLE 4

33 g of trimebutyne are added to a solution of 67 g of ursodeoxicholic acid in 500 ml of 80%-acetone. The mix is heated under agitation, until a limpid solution is obtained (about 40° C.), and the agitation is kept going at the same temperature for about 30 minutes; then it is cooled to 20° C. and 1000 ml of distilled water are slowly added, always under a strong agitation.

The crystallization is completed in 3 hours under agitation and the temperature is kept at about 10° C. The precipitation which has formed is collected on a Buchner funnel, washed with 30%-acetone, and vacuum oven dried at 50° C. 94 g of product are obtained, having the following characteristics:

$[\alpha]_{20}{}^{\cdot D}$: $+40°$ (c=2% in 99%-ethanol)

Ultimate analysis: calculated—C 71,64%, H 9,29%, N 1,19%; found—C 71,94%, H 9,18%, N 1,09%.

Experimental tests carried out both in vivo (acetic acid induced strain test, prevention of acetylcholine intestinal spasm, quality and quantity changes in the bile flow) and in vitro (ileum-jejunum-gall bladder) proved that the new compounds have a better pharmacological action compared with their components either singularly used or in simple association.

We claim:

1. A salt of a cholic acid, selected from the group consisting of chenodeoxycholic acid and ursodeoxycholic acid, with the trimethoxy-3,4,5-benzoic ester of 2-phenyl-2-dimethylaminobutanol.

2. A salt according to claim 1, in which cholic acid and the trimethoxy-3,4,5-benzoic ester of 2-phenyl-2-dimethylaminobutanol are present in the molar ratio 1:1.

3. A salt according to claim 1, in which cholic acid and the trimethoxy-3,4,5-benzoic ester of 2 -phenyl-2-dimethylaminobutanol are present in the molar ratio 2:1.

4. Process for the production of salts of cholic acid, selected from the group consisting of chenodeoxycholic acid and the ursodeoxycholic acid with the trimethoxy-3,4,5-benzoic ester of the 2-phenyl-2-dimethylaminobutanol, characterized by the fact that the cholic acid and the trimethoxy-3,4,5-benzoic ester of 2-phenyl-2-dimethylaminobutanol are reacted, in the desired stoichiometric ratios in a polar solvent, at temperatures ranging from 40° to 100° C., and the salt so formed is precipitated.

5. Process according to claim 4, in which the formed salt is precipitated by vacuum concentration and cooling.

6. Process according to claim 4, in which the formed salt is precipitated by means of dilution with water, a poorly polar solvent or their mixtures, and elimination of the solvent.

7. Process according to claim 4, in which cholic acid and the trimethoxy-3,4,5-benzoic ester of 2-phenyl-2-dimethylaminobutanol are reacted in a molarity ratio 1:1.

8. Process according to claim 4, in which the cholic acid and the trimethoxy-3,4,5-benzoic ester of 2-phenyl-2-dimethylaminobutanol are reacted in a molarity ratio 2:1.

9. Process according to claim 4, in which the polar solvents are selected from the group consisting of water, tetrahydrofuran, methyl alcohol, ethanol, acetone, isopropyl, alcohol, 1,4-dioxane and mixtures thereof.

10. Process according to claim 6, in which poorly polar solvents are selected from the group consisting of aliphatic $C_5$–$C_8$ hydrocarbons.

11. A therapeutic composition for the treatment of diskinesiae, biliary dyspepsiae, cholecystopathies, and for the normalization of the gastro-biliary tract kinesis, comprising a therapeutically effective amount of a salt of a cholic acid, selected from the group consisting of chenodeoxycholic acid and ursodeoxycholic acid, with the trimethoxy-3,4,5-benzoic ester of 2-phenyl-2-dimethylaminobutanol, in the molar ratio 1:1 or 2:1, and a pharmaceutically acceptable carrier.

* * * * *

UNITED STATES PATENT AND TRADEMARK OFFICE
CERTIFICATE OF CORRECTION

PATENT NO. : 4,404,199
DATED : September 13, 1983
INVENTOR(S) : Antonio BONALDI et al It is certified that error appears in the above—identified patent and that said Letters Patent is hereby corrected as shown below:

In the Heading of the patent, the title should be amended to read:

-- [54] SALIFICATION PRODUCTS OF CHOLIC ACIDS WITH TRIMETHOXY-3,4,5-BENZOIC ESTER OF 2-PHENYL-2-DIMETHYLAMINOBUTANOL, HAVING PHARMACOTHERAPEUTIC ACTION, PROCESS FOR THEIR PREPARATION AND THERAPEUTIC COMPOSITIONS CONTAINING THEM AS ACTIVE PRINCIPLE --.

Signed and Sealed this

Seventeenth Day of July 1984

[SEAL]

Attest:

GERALD J. MOSSINGHOFF

Attesting Officer

Commissioner of Patents and Trademarks